(12) United States Patent
Matsumoto

(10) Patent No.: US 8,551,007 B2
(45) Date of Patent: Oct. 8, 2013

(54) PULSE RATE MEASURING APPARATUS

(75) Inventor: Chikako Matsumoto, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1063 days.

(21) Appl. No.: 12/367,251

(22) Filed: Feb. 6, 2009

(65) Prior Publication Data

US 2009/0287099 A1    Nov. 19, 2009

(30) Foreign Application Priority Data

May 15, 2008  (JP) ................................. 2008-128573

(51) Int. Cl.
*A61B 5/02*    (2006.01)

(52) U.S. Cl.
USPC ............ 600/500; 600/502; 600/504; 600/508

(58) Field of Classification Search
None
See application file for complete search history.

(56) References Cited

U.S. PATENT DOCUMENTS 6,360,888 B1 *   3/2002   McIvor et al. ................ 206/305
2009/0124914 A1 *   5/2009   Kuo et al. ..................... 600/500

FOREIGN PATENT DOCUMENTS

| JP | 1-190335 | 7/1989 |
|---|---|---|
| JP | 2001-198094 | 7/2001 |
| JP | 2001-353132 | 12/2001 |
| JP | 2002-330935 | 11/2002 |
| JP | 2004-121625 | 4/2004 |
| JP | 2004-150280 | 5/2004 |

* cited by examiner

*Primary Examiner* — Benjamin P Blumel
(74) *Attorney, Agent, or Firm* — Staas & Halsey LLP

(57) ABSTRACT

From pulse wave data obtained from change in a blood flow, an average interval of a prescribed number of immediately preceding pulses or pulses in an immediately preceding prescribed time period is calculated. Next, an average-calculation range is determined on the basis of at least one of an amount of fluctuation and an evaluation result. The amount of fluctuation is a value calculated on the basis of a difference between the average interval and an interval of a pulse wave newly detected from the pulse wave data. The evaluation result is a result of evaluating the interval of the newly detected pulse wave by at least one evaluation factor. Thereafter, an average pulse wave interval value is calculated by averaging pulse wave intervals on the basis of the average-calculation range, and a pulse rate is calculated on the basis of the average pulse wave interval value.

9 Claims, 16 Drawing Sheets

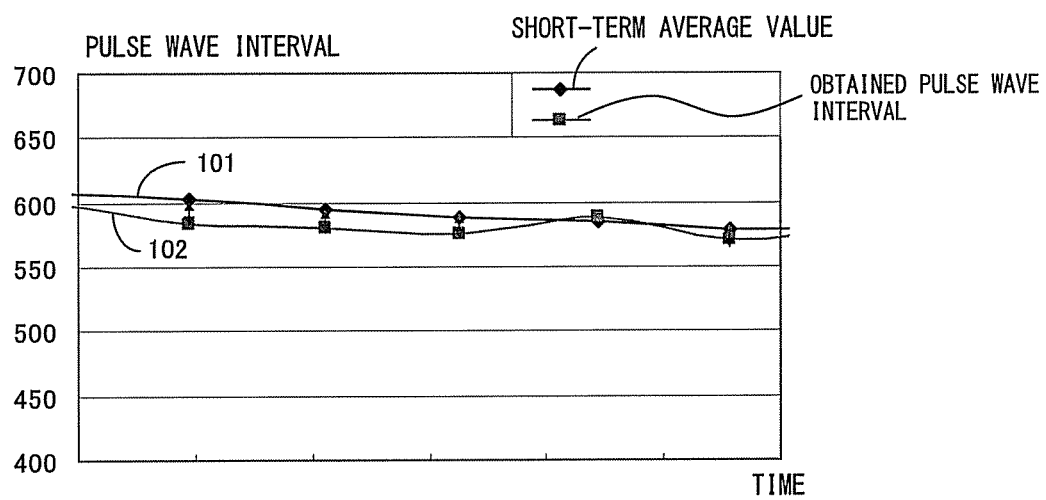
F I G. 1

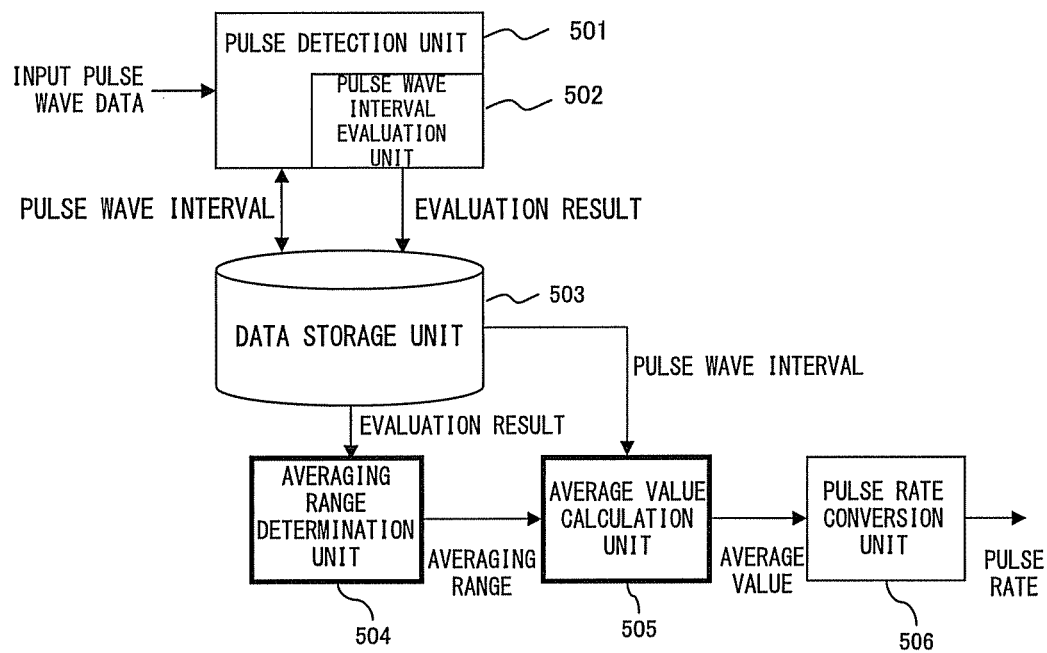
F I G. 5

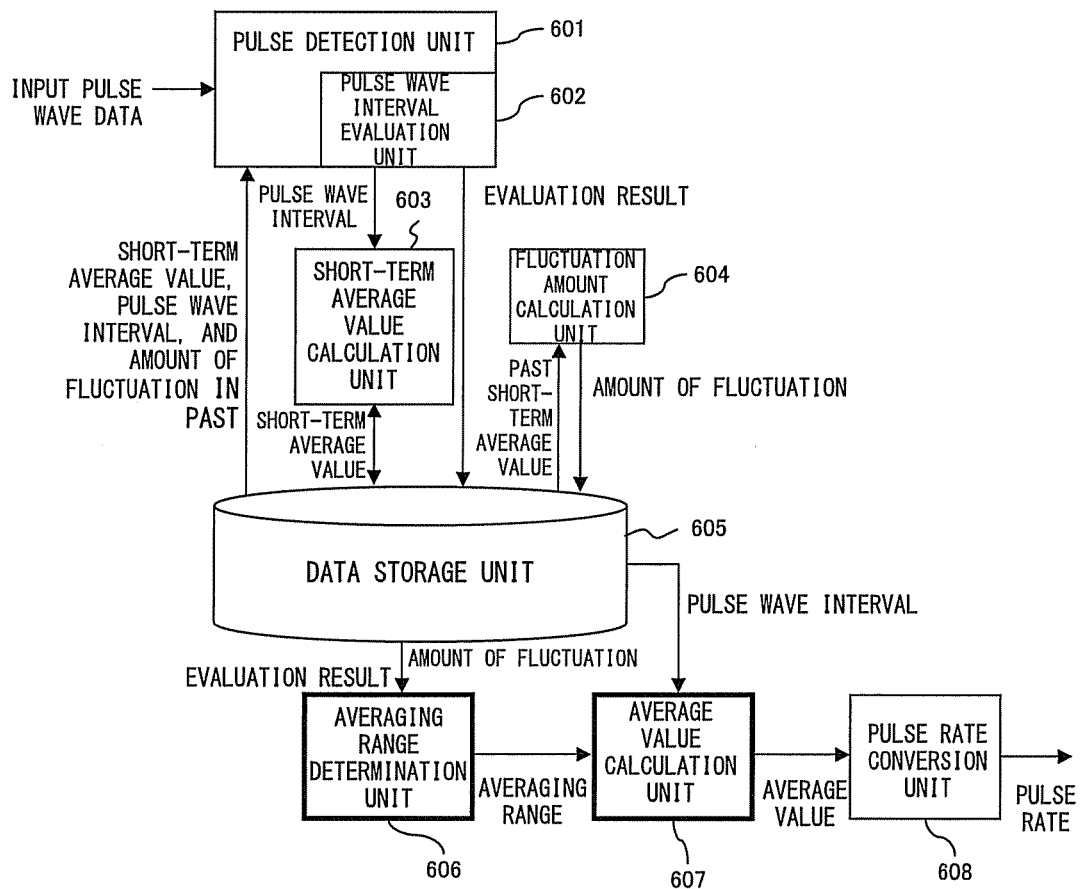
F I G. 6

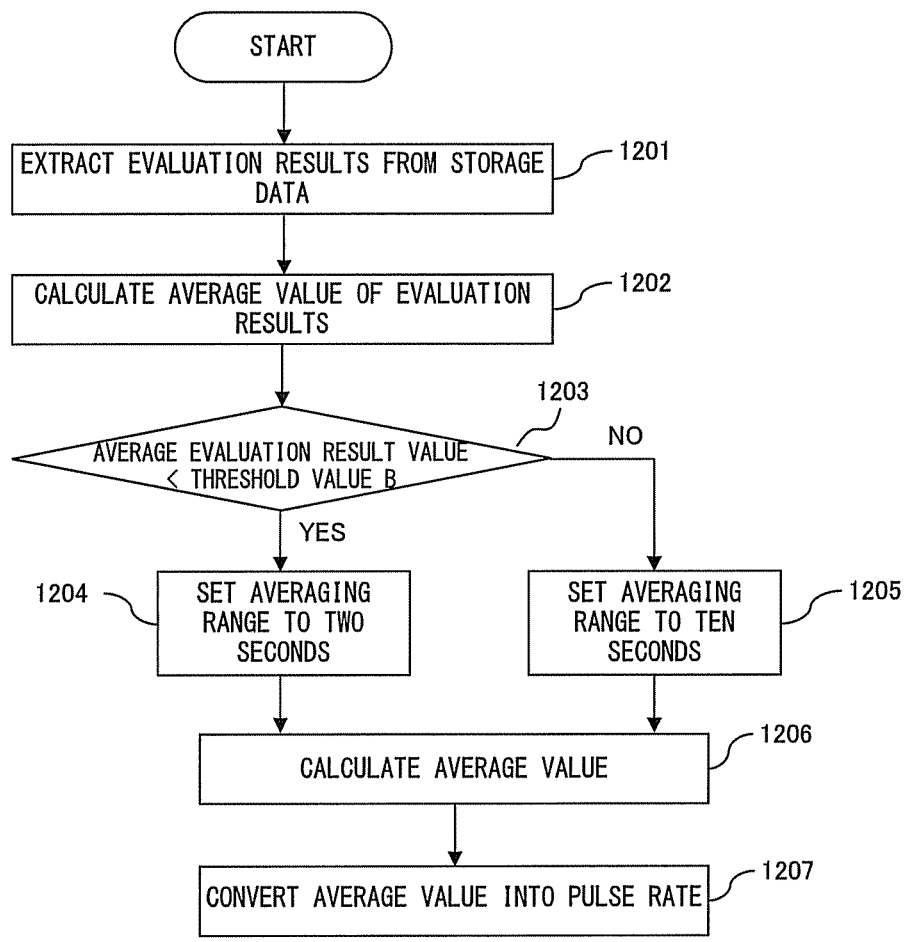
F I G. 1 2

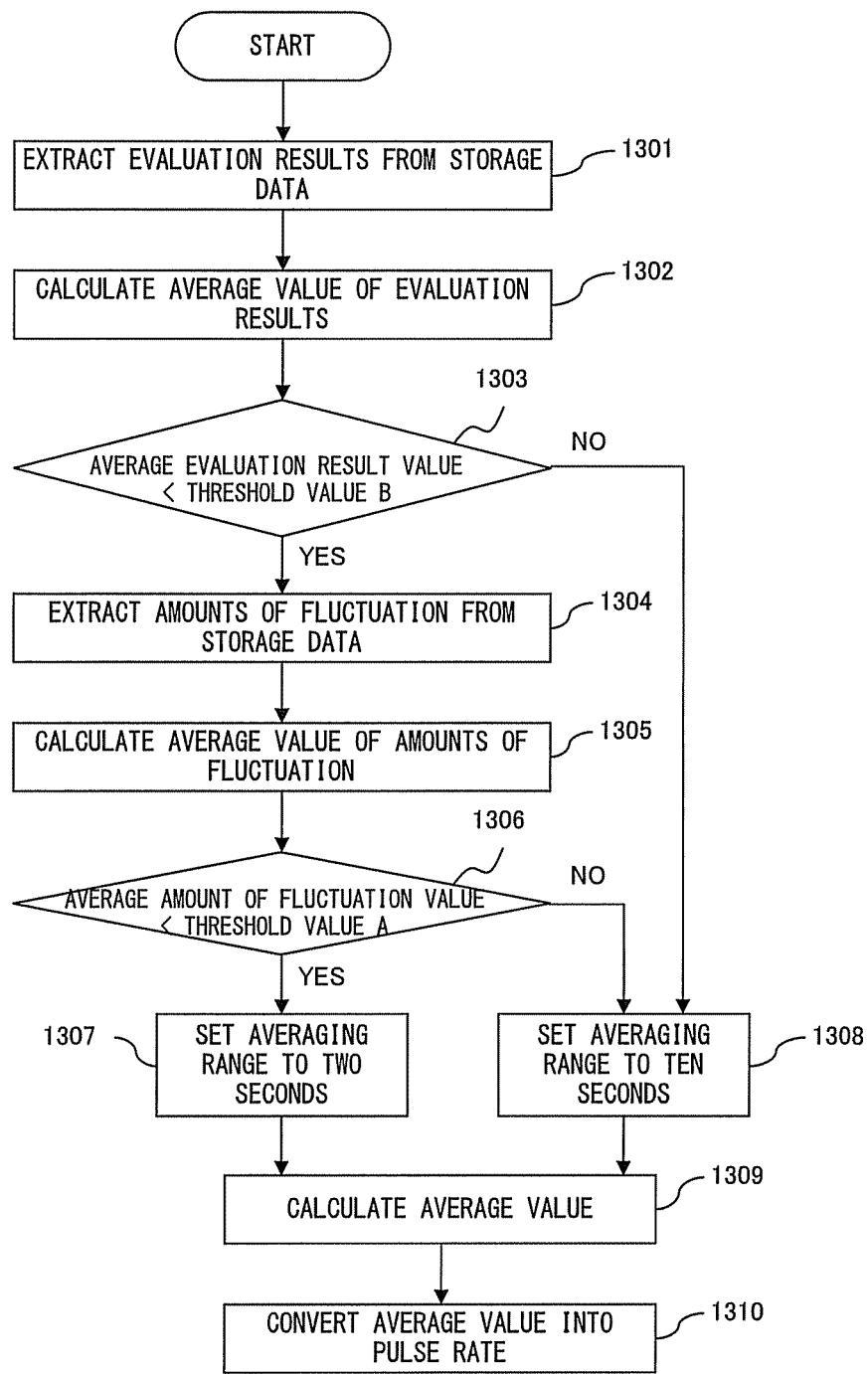
F I G. 13

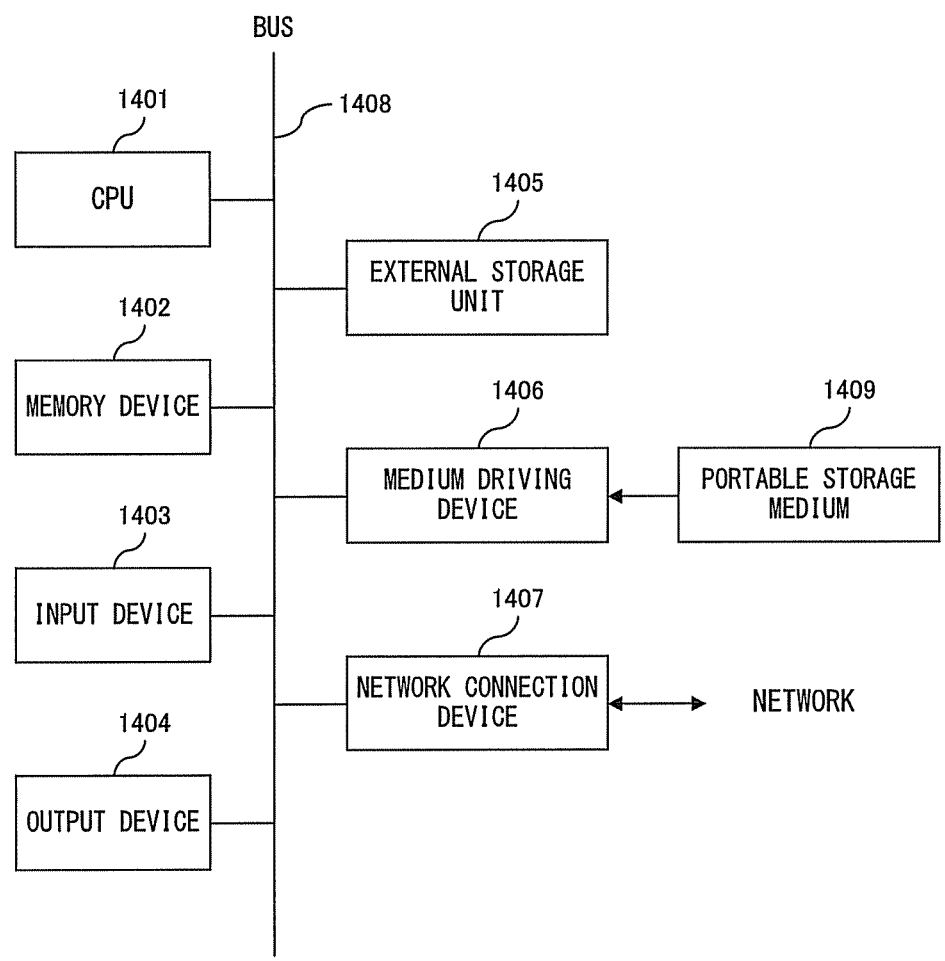
F I G. 14

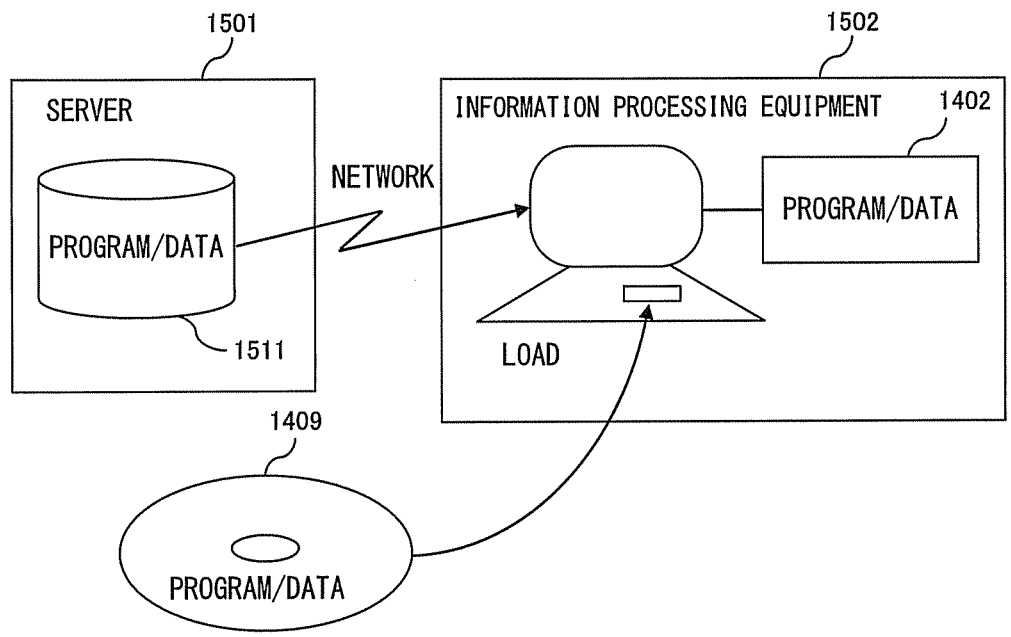
F I G. 1 5

PULSE RATE MEASURING APPARATUS

CROSS-REFERENCE TO RELATED APPLICATIONS

This application is based upon and claims the benefit of priority of the prior Japanese Patent Application No. 2008-128573, filed on May 15, 2008, the entire contents of which are incorporated herein by reference.

FIELD

The embodiments discussed herein are related to a pulse rate measuring apparatus for obtaining a pulse rate from pulse wave data obtained on the basis of changes in a blood flow.

BACKGROUND

For detection of pulse waves, various methods including a method by which a heart rate is obtained by directly detecting results of electrocardiographic monitoring and a method by which a blood flow pitch is measured on the basis of the reflection light or transmitted light obtained by irradiating a blood vessel with light are used. The latter method imposes less burden of wearing the equipment on the examinees.

As a conventional method of measuring pulse rates, a method in which an average of input signals is calculated in prescribed units and a Fourier transform is performed on the resultant value is known. This method permits accurate measurement of pulse rates even with operation means of a low computing capacity.

As a conventional method relating to electronic sphygmomanometers, a method in which only limited heart rates are used for calculating an average of pulse wave pitches is known. In this method, it is determined whether or not a pulse wave pitch of a newly obtained pulse wave is equal to the average pulse wave pitch, and a counter value is incremented when it is not equal. When the counter value has reached a prescribed value, generation of too much noise is recognized and a signal reporting this fact is transmitted.

Further, as a conventional method of smoothing waveforms, a method in which $\epsilon$ filter is used is known. In this method, an average value is used for reducing fluctuation when the waveform is in a stationary state, and when the waveform is in a transient state, the waveform itself is output in order to eliminate phase delays.

Patent Document 1:
  Japanese Laid-open Patent Publication No. 2004-121625
Patent Document 2:
  Japanese Laid-open Patent Publication No. 01-190335
Patent Document 3:
  Japanese Laid-open Patent Publication No. 2004-150280

SUMMARY

According to an aspect of the invention, a pulse rate measuring apparatus includes first through third calculation devices and a determination device.

The first calculation device receives input of pulse wave data obtained from change in a blood flow, and calculates an average interval of a prescribed number of immediately preceding pulses or pulses in an immediately preceding prescribed time period.

The determination device determines an average-calculation range for calculating an average value on the basis of at least one of an amount of fluctuation and an evaluation result. The amount of fluctuation is a value calculated on the basis of a difference between the average interval and an interval of a pulse wave newly detected from the pulse wave data. The evaluation result is a result of evaluating the interval of the newly detected pulse wave by at least one evaluation factor.

The second calculation device averages pulse wave intervals of the pulse wave data on the basis of the average-calculation range, and calculates an average pulse wave interval value. The third calculation device calculates a pulse rate on the basis of the average pulse wave interval value.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 1 illustrates changes in pulse wave intervals when the examinee is staying quiet;

FIG. 5 illustrates a configuration of a second pulse rate measuring apparatus;

FIG. 6 illustrates a configuration of a third pulse rate measuring apparatus;

FIG. 12 is a flowchart for a third averaging range determination process;

FIG. 13 is a flowchart for a fourth averaging range determination process;

FIG. 14 illustrates a configuration of information processing equipment;

FIG. 15 illustrates a manner of providing programs and data; and

DESCRIPTION OF EMBODIMENTS

When a pulse is detected from the a pulse wave with the examinee staying quiet or walking, fluctuation caused by errors involved in the detected pulse is small because the pulse wave is less disturbed. However, when a pulse is detected with the examinee exercising i.e., running, etc., fluctuation in the detected pulse is large because of a greater disturbance in the pulse wave. When the examinee is staying quiet or walking, slight variations can easily occur in the pulse rates although fluctuation caused by errors in the detected pulse is small.

When a pulse wave sensor used for detecting a pulse of an exercising person follows disturbances in the pulse, the detected pulse rates vary frequently, resulting in inconvenience to users. In order to cope with this inconvenience, an average pulse rate in a prescribed range is calculated in order to reduce influences by such disturbances. However, when a range for averaging (averaging range) is too wide, outputs of pulse rates are delayed from the actual pulsing motions. Accordingly, when an average value of the pulse detected under different conditions (exercising, staying quiet, and walking) is calculated using the same averaging range as in conventional methods, an imprecise pulse rate is output and displayed.

Figure 16:
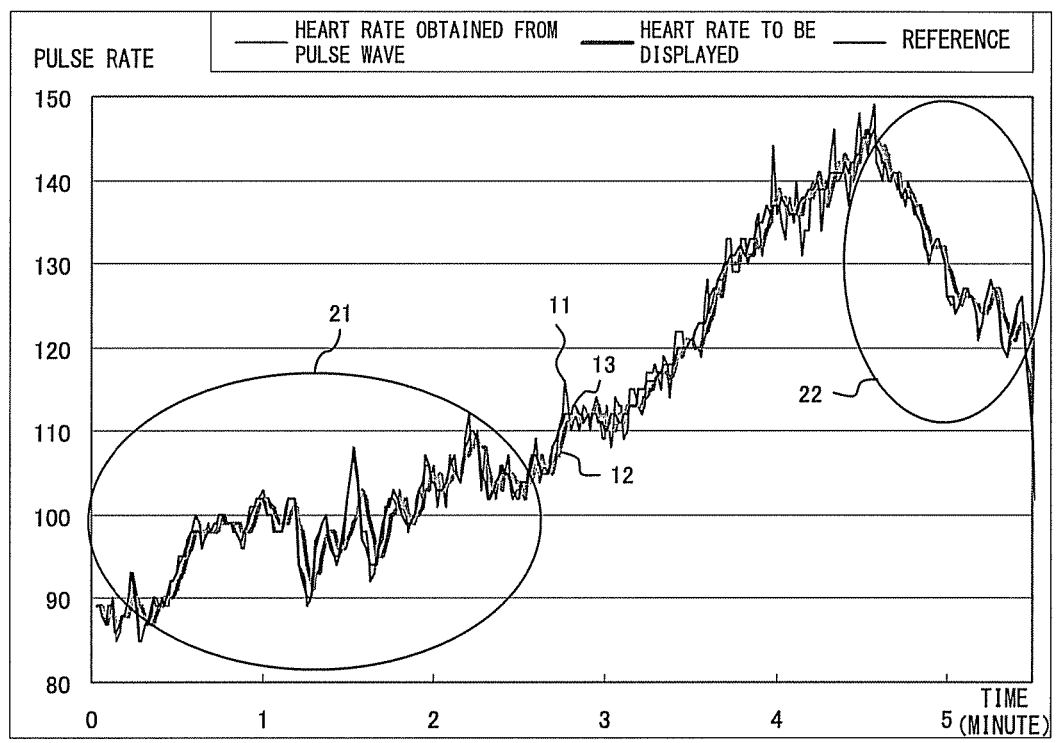
FIG. 16 illustrates average pulse rates obtained using a constant averaging range.

FIG. 16 illustrates an example of changes occurring as time elapses in average pulse rates obtained in the above averaging process. Curve 11 represents the pulse rates obtained from pulse wave data. Curve 12 represents the pulse rates to be displayed (display pulse rates) obtained through an averaging process using a constant averaging range. Curve 13 represents heart rates detected directly from results of electrocardiographic monitoring (reference).

As in periods 21 and 22, when the examinee is staying quiet and the variations can easily occur in the heart rates, curve 11 involves large delay or the peaks and valleys appear close to each other so as to make themselves indistinct (variations in the pulse cannot be expressed accurately). When the examinee is exercising i.e., the waveform of the pulse wave is greatly disturbed, fluctuation remains in the case of a narrow averaging range (disturbances in the pulse influence the measurement result).

When an examinee is exercising strenuously, the pulse wave is often disturbed greatly even in a transient state because of movements of the body of the examinee or the sensor moved from the original position, etc. In a transient state, when great disturbance occurs, values obtained through averaging over a relatively long period are more likely to correspond to the actual pulse wave. Accordingly, when a pulse is to be detected from a pulse wave, it is not appropriate to determine whether or not to perform an averaging process on the basis only of the waveform as in the ϵ filtering.

Preferred embodiments of the present invention will be explained with reference to accompanying drawings.

When a pulse rate is detected from pulse wave data, a disturbance in the pulse wave data is estimated, and the level of smoothing the pulse rates is controlled on the basis of the result of the estimation. Estimation of a disturbance in pulse data uses changes in pulse wave intervals occurring depending on the levels of disturbances in the pulse wave.

FIG. 1 illustrates an example of changes occurring as time elapses in pulse wave intervals when the examinee is staying quiet. A pulse wave interval is an interval between one pulse wave and another pulse wave that immediately precedes the pulse wave, and is expressed in the form of, for example, a cycle number of a sampling clock.

Figure 2:
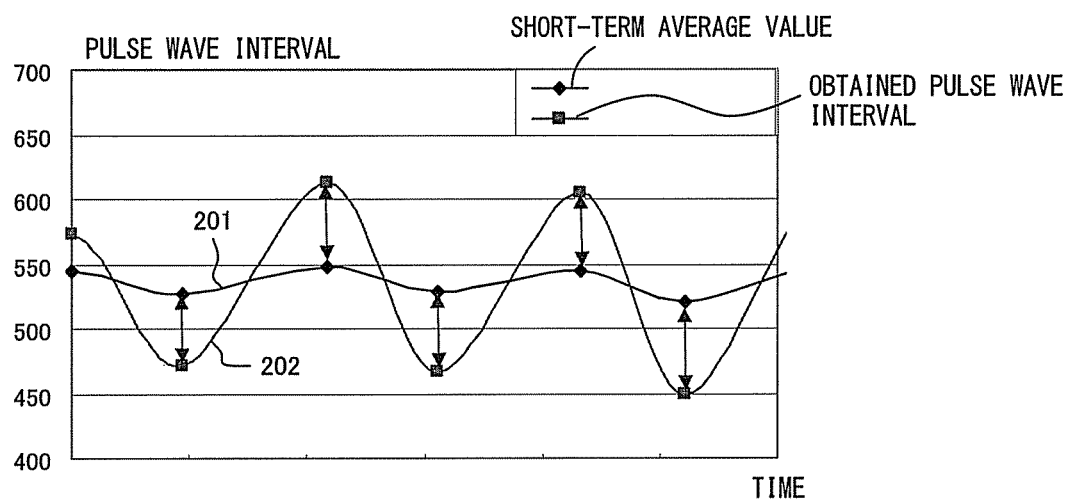
FIG. 2 illustrates changes in pulse wave intervals when the examinee is exercising.

Curve 101 illustrated in FIG. 1 represents short-term average values of the pulse wave intervals. Curve 102 represents pulse wave intervals that are detected newly. FIG. 2 illustrates an example of changes occurring as time elapses in pulse wave intervals when the examinee is exercising. Curve 201 represents short-term averages of pulse wave intervals. Curve 202 represents pulse wave intervals that are detected newly.

Comparison between FIGS. 1 and 2 indicates that the gaps between the newly detected pulse wave intervals and the short-term average values in case with the examinee staying quiet are different from the gaps between them in case with the examinee exercising. Detection of this difference enables estimation of levels of disturbances of pulse waves. Further, the pulse wave intervals obtained when detecting the pulse wave intervals from the pulse wave data are evaluated in order to obtain the disturbances of the pulse waves more accurately.

The average-calculation range used for calculating an average value (averaging range) in the smoothing is determined on the basis of thus obtained result of estimating pulse wave disturbances, and thereby smoothing in response to the pulse wave disturbances is performed. When pulse wave disturbances are large, a relatively wide averaging range is used in order to reduce the influence of the disturbances. When pulse wave disturbances are small, a relatively narrow averaging range is used in order to shorten delay time. Thereby, in both cases with large and small pulse wave disturbances, a pulse rate as close to the actual value as possible can be output.

Figure 3:
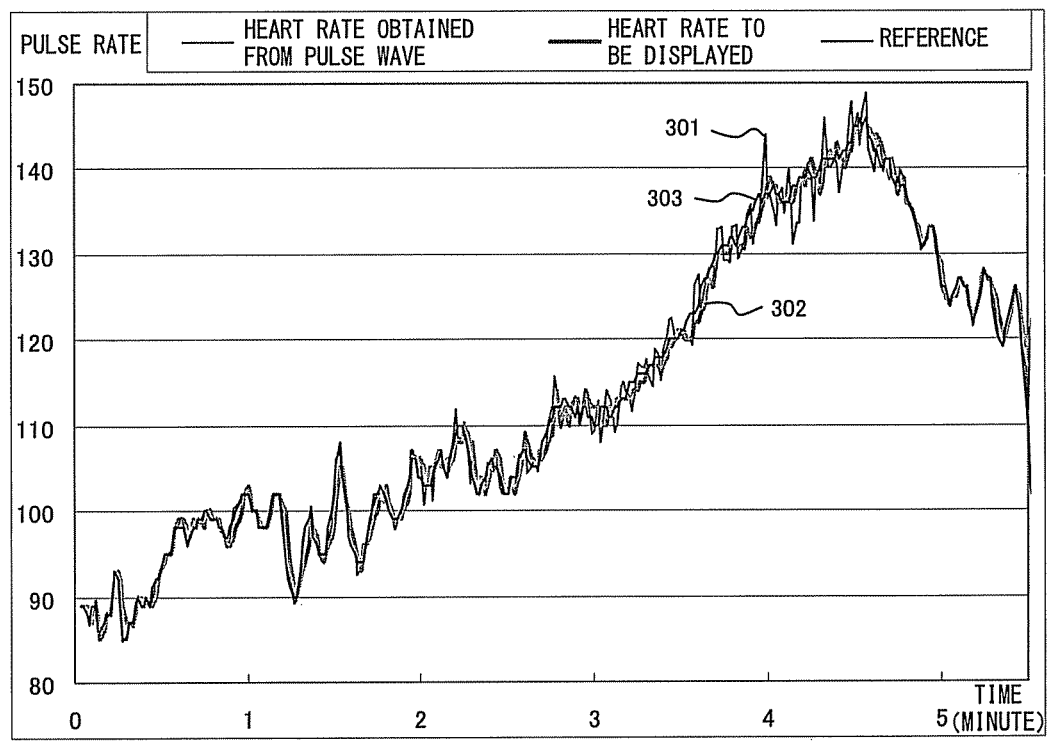
FIG. 3 illustrates average pulse rates obtained using a variable averaging range.

FIG. 3 illustrates an example of changes occurring as time elapses in average pulse rates obtained in the above averaging process. Curve 301 represents changes in pulse rates obtained from the pulse wave data. Curve 302 represents changes in pulse rates to be displayed (display pulse rates), obtained through averaging with a constant averaging range. Curve 303 represents changes in heart rates detected directly from results of electrocardiographic monitoring (reference).

In this case, curves 302 and 303 well correspond to each other over the entire period. When compared with FIG. 16, it is understood that more accurate display pulse rates are calculated.

Next, a configuration and operations of a pulse rate measuring apparatus will be explained specifically by referring to FIGS. 4 through 13. Pulse wave data is input into the pulse rate measuring apparatus from, for example, a pulse wave sensor. The pulse rate measuring apparatus outputs to a display device processing results such as pulse wave intervals, pulse rates, and the like. The pulse rate measuring apparatus outputs data also to devices in subsequent stages that are connected to the pulse rate measuring apparatus.

Figure 4:
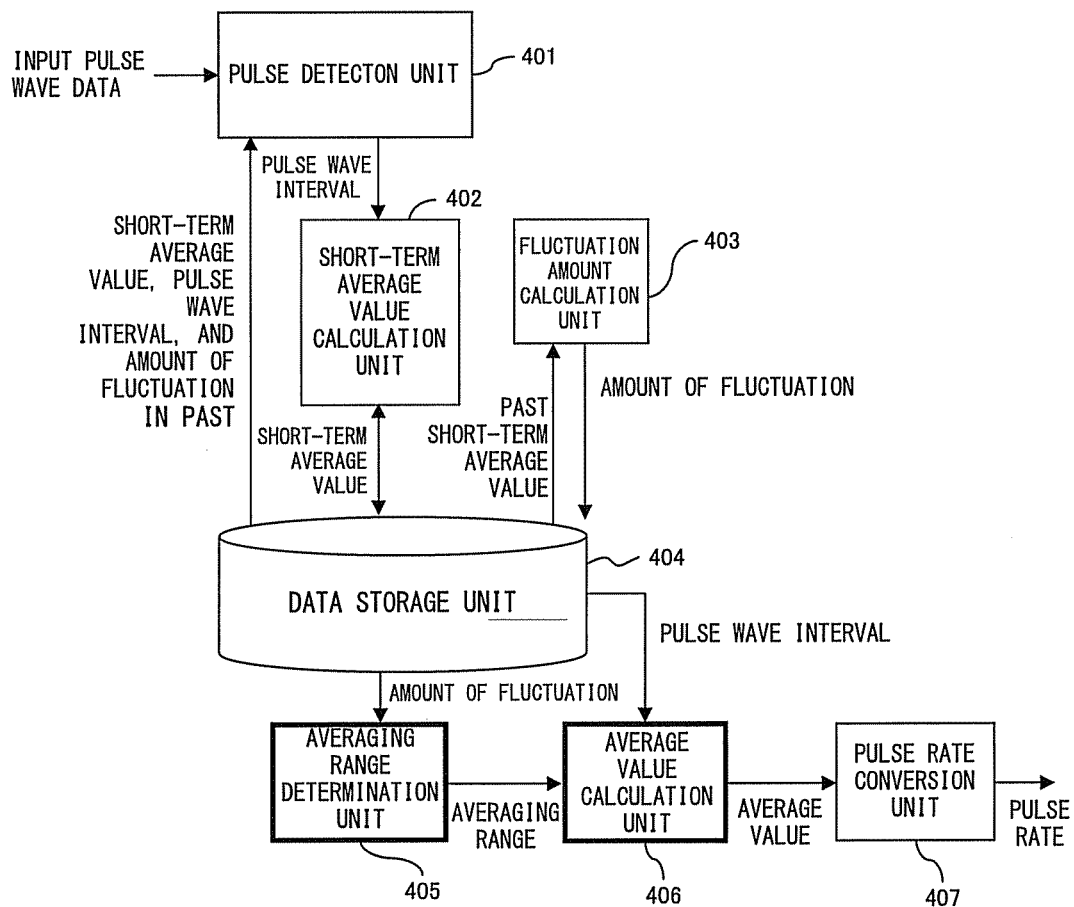
FIG. 4 illustrates a configuration of a first pulse rate measuring apparatus.

FIG. 4 illustrates an example of a configuration of the pulse rate measuring apparatus for estimating disturbances of pulse waves on the basis of the amount of fluctuation. This pulse rate measuring apparatus includes a pulse detection unit 401, a short-term average value calculation unit 402, a fluctuation amount calculation unit 403, a data storage unit 404, an averaging range determination unit 405, an average value calculation unit 406, and a pulse rate conversion unit 407. The data storage unit 404 stores pulse wave intervals, short-term average values of pulse wave intervals, and amounts of fluctuation.

With pulse wave data input into the pulse detection unit 401, the pulse detection unit 401 detects a pulse wave interval from the pulse wave data on the basis of the short-term average value, pulse wave interval, and amount of fluctuation in the past stored in the data storage unit 404. The detected pulse wave interval is output to the short-term average value calculation unit 402. The short-term average value calculation unit 402 calculates a short-term average value by averaging the pulse wave intervals of a prescribed number of pulses (for example, several pulses or pulses in a prescribed time period) that immediately precede the detected pulse wave interval. The detected pulse wave interval and the calculated short-term average value are stored in the data storage unit 404.

From the absolute value of the difference between the past short-term average value stored in the data storage unit 404 and the value of the detected pulse wave interval, the fluctuation amount calculation unit 403 calculates the amount of fluctuation corresponding to the disturbance in the pulse wave data. The calculated amount of fluctuation is stored in the data storage unit 404.

The graph illustrated in FIG. 1 indicates a case with less disturbance. The graph illustrated in FIG. 2 indicates a case with many disturbances. Fluctuation amount (i) at time i is calculated by using short-term average value (i) and detected pulse wave interval (i) at time i, i.e., for example by accumulating the results of |short-term average value (i)−pulse wave interval (i)| for a prescribed period. Accordingly, the case illustrated in FIG. 1 produces small amounts of fluctuation, and the case illustrated in FIG. 2 produces great amounts of fluctuation.

On the basis of the amount of fluctuation stored in the data storage unit 404, the averaging range determination unit 405 obtains an averaging range corresponding to the number of pulse wave intervals used for obtaining an average value of pulse wave intervals. With a greater amount of fluctuation, the averaging region is wider, and with a smaller amount of fluctuation, the averaging region is narrower.

The average value calculation unit 406 obtains the average value by averaging the pulse wave intervals in the averaging range, and outputs the obtained average value to the pulse rate conversion unit 407. The pulse rate conversion unit 407 converts the average value of the pulse wave intervals into a pulse rate on the basis of the sampling frequency of the pulse wave data.

FIG. 5 illustrates an example of a configuration of a pulse rate measuring apparatus for estimating a pulse wave disturbance on the basis of a result of evaluating pulse wave intervals. This pulse rate measuring apparatus includes a pulse detection unit 501, a data storage unit 503, an averaging range determination unit 504, an average value calculation unit 505, and a pulse rate conversion unit 506. The pulse detection unit 501 includes a pulse wave interval evaluation unit 502. The data storage unit 503 stores pulse wave intervals and evaluation results.

With pulse wave data input into the pulse detection unit 501, the pulse detection unit 501 detects a pulse wave interval from the pulse wave data on the basis of past pulse wave intervals stored in the data storage unit 503. The detected pulse interval is stored in the data storage unit 503.

The pulse wave interval evaluation unit 502 evaluates the detected pulse wave interval. The pulse wave interval evaluation unit 502 obtains, as a result of evaluating a pulse wave interval, a minimum value (or a maximum value) when, for example, a search for a pulse wave interval is to be made using a minimum value (or a maximum value) of the input waveform. When a search for a pulse wave interval is to be made using the autocorrelation of the input waveform, the pulse wave interval evaluation unit 502 obtains the correlation value as a result of evaluation. When a pulse rate of an examinee in a normal state is stored in the data storage unit 503, information on a difference between the pulse wave interval and the pulse rate of the examinee in the normal state is added to the result of evaluation. The obtained evaluation result is stored in the data storage unit 503.

The averaging range determination unit 504 obtains an averaging range on the basis of evaluation results stored in the data storage unit 503. For a worse result of evaluating a pulse wave interval, a wider averaging range is obtained, and for a better result of evaluating a pulse wave interval, a narrower averaging range is obtained.

The processes executed by the average value calculation unit 505 and the pulse rate conversion unit 506 are similar to those executed by the average value calculation unit 406 and the pulse rate conversion unit 407 illustrated in FIG. 4.

FIG. 6 illustrates an example of a configuration of a pulse rate measuring apparatus for estimating a disturbance in a pulse wave on the basis of a result of evaluating an amount of fluctuation and a pulse wave interval. This pulse rate measuring apparatus includes a pulse detection unit 601, a pulse wave interval evaluation unit 602, a short-term average value calculation unit 603, a fluctuation amount calculation unit 604, a data storage unit 605, an averaging range determination unit 606, an average value calculation unit 607, and a pulse rate conversion unit 608. The data storage unit 605 stores a pulse wave interval, a short-term average value of the pulse wave intervals, an amount of fluctuation, and a result of evaluation.

With pulse wave data input into the pulse detection unit 601, the pulse detection unit 601 detects a pulse wave interval from the pulse wave data on the basis of a short-term average value, pulse wave interval, and amount of fluctuation in the past stored in the data storage unit 605. The detected pulse wave interval is output to the short-term average value calculation unit 603.

The processes executed by the pulse wave interval evaluation unit 602 are similar to those executed by the pulse wave interval evaluation unit 502 illustrated in FIG. 5. The processes executed by the short-term average value calculation unit 603, the fluctuation amount calculation unit 604, the average value calculation unit 607, and the pulse rate conversion unit 608 are similar to those executed by the short-term average value calculation unit 402, the fluctuation amount calculation unit 403, the average value calculation unit 406, and the pulse rate conversion unit 407 illustrated in FIG. 4.

The averaging range determination unit 606 obtains an averaging range from the amount of fluctuation and the evaluation result stored in the data storage unit 503. For a larger amount of fluctuation, a wider averaging range is obtained, and for a smaller amount of fluctuation, a narrower averaging range is obtained. Also, for a worse result of evaluating a pulse wave interval, a wider averaging range is obtained, and for a better result of evaluating a pulse wave interval, a narrower averaging range is obtained.

As illustrated in FIGS. 4 through 6, a disturbance in a pulse wave is expressed as an amount of fluctuation or a result of evaluation, and an averaging range is determined on the basis of the amount of fluctuation or the result of evaluation, and thereby a wide averaging range can be used in order to suppress influences of a disturbance when there is a great disturbance in a pulse wave. When a disturbance in a pulse wave is small, a narrow averaging range is used so that delay time (a time period between an actual pulsing motion and the time point at which the measured value is output as a value to be displayed after being processed in the pulse rate measuring apparatus) can be reduced.

Figure 7:
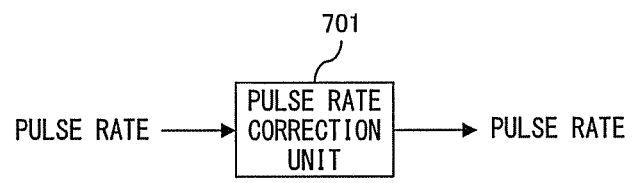
FIG. 7 illustrates a pulse rate correction unit.

FIG. 7 illustrates a pulse rate correction unit 701, which is to be added in a stage subsequent to the pulse rate conversion unit 407, the pulse rate conversion unit 506, or the pulse rate conversion unit 608 respectively illustrated in FIGS. 4 through 6. The pulse rate correction unit 701 corrects a pulse rate output from the pulse rate conversion unit 407, the pulse rate conversion unit 506, or the pulse rate conversion unit 608 in order to prevent the changing ratio of an averaged pulse interval from becoming extremely high, and thereafter outputs the corrected pulse rate.

Figure 8:
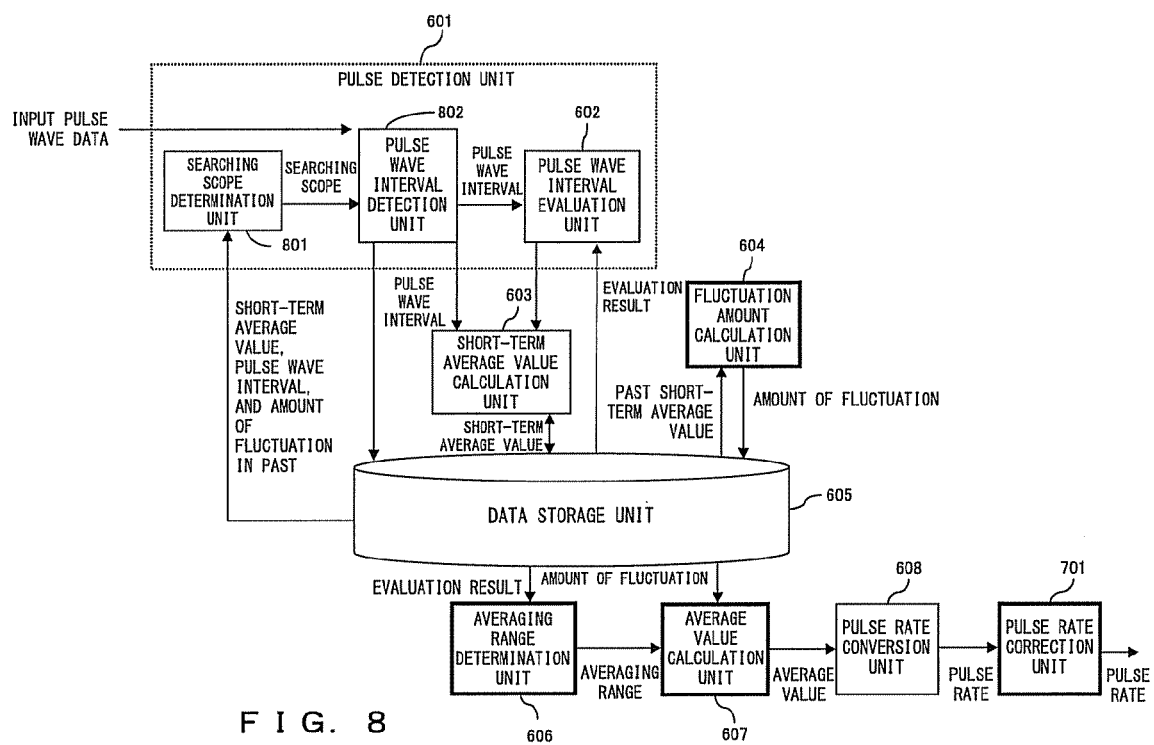
FIG. 8 illustrates a configuration of a fourth pulse rate measuring apparatus.

FIG. 8 illustrates an example of a configuration obtained by adding the pulse rate correction unit 701 illustrated in FIG. 7 to the pulse rate measuring apparatus illustrated in FIG. 6. The pulse detection unit 601 includes a searching scope determination unit 801, a pulse wave interval detection unit 802, and a pulse wave interval evaluation unit 602.

The pulse detection unit 601 detects a pulse wave interval from pulse wave data. Hereinafter, the expression "AAI(i)" is used to express the pulse wave interval at time i. The searching scope determination unit 801 refers to a short-term average value, pulse wave interval, and amount of fluctuation in the past stored in the data storage unit 605 in order to determine a scope in which a search for a pulse wave interval is to be made (searching scope).

A scope obtained by, for example, shifting a "width of searching scope" by a "shifting length" around the center value of a pulse wave interval expectation value is set as a searching scope. A value such as a short-term average value, a pulse wave interval obtained immediately before, or the like is used as a pulse wave interval expectation value. The width of a searching scope at time i is calculated using an amount of fluctuation and the pulse wave interval AAI(i−1) obtained immediately before, specifically by the equation below.

$$\text{width of searching scope} = AAI(i-1) \times 0.5 \times (1 + \text{fluctuation amount}) \quad (1)$$

A shifting length is calculated using short-term average value (i) at time i and short-term average value (i−1), which was obtained immediately before that, specifically by the equation below.

$$\text{shifting length} = (\text{short term average value } (i) - \text{short term average value } (i-1)) \times \alpha \quad (2)$$

In the above equation, α is a coefficient ranging approximately between 0.1 and 0.5. Under these conditions, a searching scope is set using the equation below.

$$\text{searching scope} = (\text{pulse wave interval expectation value} + \text{shifting length}) \pm \text{width of searching scope} \quad (3)$$

The pulse wave interval detection unit 802 obtains a detection point, which serves as a reference for pulse wave intervals in the determined searching scope. Thereafter, the pulse wave interval detection unit 802 outputs the interval between the detection points that were obtained previously and currently, to the pulse wave interval evaluation unit 602, the short-term average value calculation unit 603, and the data storage unit 605. This interval is output as a pulse wave interval. Detection points are obtained, for example, by the methods below.

(a) The position corresponding to the minimum (or maximum) value in pulse wave data is obtained as a detection point.
(b) The position corresponding to the minimum (or maximum) value in difference data of pulse wave data is obtained as a detection point.
(c) The position corresponding to the minimum (or maximum) value in secondary difference data of pulse wave data is obtained as a detection point.
(d) The autocorrelation of pulse wave data is obtained, and the position corresponding to the maximum value of the correlation value is obtained as a detection point. For example, when the pulse wave data is made of discrete signals, the autocorrelation is calculated by the equation below, in which the value of the N-th signal is $x_N$, and the lag is j.

$$R_{xx}(j) = \frac{1}{(N-j)} \sum_{i=1}^{N-1-j} x_i x_{i+j} \quad (j = 0, 1, 2, \ldots, N-1) \quad (4)$$

(e) The autocorrelation of the difference data of pulse wave data is obtained, and the position corresponding to the maximum value of the correlation value is obtained as a detection point.
(f) The autocorrelation of the secondary difference data of pulse wave data is obtained, and a position corresponding to the maximum value of the correlation value is obtained as a detection point.

In addition, difference data and secondary difference data described herein are time difference data of pulse wave data. For example, when pulse wave data is d(t), difference data d'(t) can be expressed by d'(t)=d(t)−d(t−1), and secondary difference data d''(t) can be expressed by d''(t)=d'(t)−d'(t−1).

When the above minimum value, maximum value, correlation value or the like at a detection point is to be used for evaluating a pulse wave interval, these values are output to the pulse wave interval evaluation unit 602 as well.

The short-term average value calculation unit 603 averages the pulse wave intervals of a prescribed number of pulses that immediately precede the detected pulse wave interval in order to calculate a short-term average value. For example, when n pulse intervals in the past are used, short-term average value (i) is calculated by the equation below.

$$\text{short-term average value}(i) = \left( \sum_{j=1}^{n} AAI(i-j) \right) \bigg/ n \quad (5)$$

The fluctuation amount calculation unit 604 uses a short-term average value and pulse wave interval in the past in order to calculate an amount of fluctuation using, for example, the equation below.

$$\text{fluctuation amount} = \quad (6)$$

$$\left( \sum_{j=1}^{n} \frac{|\text{short-term average value}(i-j) - AAI(i-j)|}{\text{short-term average value}(i-j)} \right) \bigg/ n$$

For the value n in above equations (5) and (6), a constant (for instance 5) may be used, or alternatively a dynamic value (for instance the pulse rate in two seconds as a prescribed time period in the past) may be used.

An amount of fluctuation can also be calculated as a changing ratio of the sign of a value of (short-term average value (k)−AAI(k)). In such a case, the number of times that the sign has changed is counted by, for example, recognizing (short-term average value (k)−AAI (k)) as a positive value and (short-term average value (k+1)−AAI (k+1)) as a negative value, and an amount of fluctuation is calculated by the equation below.

$$\text{amount of fluctuation} = \text{the number of times that the sign has changed}/n \quad (7)$$

An amount of fluctuation can be obtained also from the changing ratio of pulse wave intervals. In such a case, an amount of fluctuation can be calculated by the equation below.

$$\text{amount of fluctuation} = (AAI(i) - AAI(i-1))/AAI(i) \quad (8)$$

Further, an amount of fluctuation can be calculated also by combining the above plural sorts of amounts of fluctuation. In such a case, an amount of fluctuation can be calculated by the equation below, where the p-th amount of fluctuation and weighting coefficient are p and αp. The total of the weighting coefficients is 1.

$$\text{amount of fluctuation} = \alpha 1 \times \text{fluctuation amount } 1 + \alpha 2 \times \text{fluctuation amount } 2 + \alpha 3 \times \text{fluctuation amount } 3 + \ldots \quad (9)$$

$$\alpha 1 + \alpha 2 + \alpha 3 + \ldots = 1.0 \quad (10)$$

The pulse wave interval evaluation unit 602 evaluates the detected pulse wave interval in order to determine whether or not the value of the detected pulse wave interval is appropriate. Thereafter, the pulse wave interval evaluation unit 602 stores the evaluation result in the data storage unit 605. Examples of methods of evaluating pulse wave intervals are described below. Each one of the methods below can be used solely, and also two or more of them can be used in combination.

(a) When a pulse wave interval is within a range of ±25 percent of the previously obtained pulse wave interval, "0" (meaning being good) is set as the evaluation result, and in the other cases, "1" (meaning being bad) is set as the evaluation result.

(b) When a pulse wave interval is within a range of ±15 percent of the previously obtained short-term average value, "0" is set as the evaluation result, and in the other cases, "1" is set as the evaluation result.

(c) When the minimum value at the detection point in the searching range is equal to or smaller than a threshold value (or the maximum value is equal to or greater than a threshold value), "0" is set as the evaluation result, and when the minimum value is greater than the threshold value (or the maximum value is smaller than the threshold value), "1" is set as the evaluation result.

(d) When the correlation value at the detection point is equal to or greater than a threshold value, "0" is set as the evaluation result, and when the correction value is smaller than the threshold value, "1" is set as the evaluation result.

(e) When there is another minimum value (or maximum value) at a position distant by ½ or ⅓ from either end of the range of the pulse wave interval, "1" is set as the evaluation result, and when there is not such a value, "0" is set as the evaluation result.

(f) When there is another maximum value of a correlation value at a position distant by ½ or ⅓ from either end of the range of the pulse wave interval, "1" is set as the evaluation result, and when there is not such a value, "0" is set as the evaluation result.

(g) When a difference between a pulse wave interval and an average value of pulse wave intervals is equal to or smaller than a threshold value, "0" is set as the evaluation result, and when the difference is greater than the threshold value, "1" is set as the evaluation result.

In addition, evaluation results do not always have to be expressed in binary such as "0" or "1", and can be expressed in the form of real numbers such as "minimum value that has been searched for/minimum value that has been set", a correlation value itself, etc.

When above method (g) is to be used, an average value of pulse wave intervals of the examinee in the normal state is beforehand stored in the data storage unit 605. This average value is an average value of pulse wave intervals of a prescribed number of pulses of the examinee staying quiet, and is stored as, for example, a predetermined value.

Additionally, instead of a difference of the average value of pulse wave intervals of the examinee in the normal state and a pulse wave interval, a difference ratio or a difference changing ratio may be used. When the average value of pulse wave intervals of the examinee in the normal state is AAI0, the difference ratio can be calculated by, for example, the equation below.

$$\text{difference ratio} = |AAI0 - AAI(i)|/AAI0 \quad (11)$$

When the difference ratio is equal to or smaller than a threshold value, "0" is set as the evaluation result, and when the difference ratio is greater than the threshold value, "1" is set as the evaluation result.

The difference changing ratio can be calculated, for example, from a change in n pulse wave intervals in the past, specifically by the equation below.

$$\text{difference changing ratio} = \left( \sum_{j=1}^{n} \frac{(AAI0 - AAI(i-j))}{AAI0} \right) / n \quad (12)$$

When a difference changing ratio is a positive value, "1" is set as the evaluation result, and when the difference changing ratio is a negative value, "0" is set as the evaluation result.

When there are plural evaluation standards as in the above described case, evaluation results can be produced by using such standards in combination. For example, when all the evaluation standards required to make the evaluation result "0" are met, "0" is set as the evaluation result, and when at least one of them is not met, "1" is set as the evaluation result. When there are evaluation results expressed in the form of real numbers respectively for the evaluation standards, the average value of such evaluation results is used as the evaluation result.

The averaging range determination unit 606 obtains an averaging range from the amount of fluctuation and the evaluation result. The average value calculation unit 607 obtains an average value by averaging pulse wave intervals in the averaging range.

The pulse rate conversion unit 608 converts the average value of the pulse wave intervals into a pulse rate on the basis of the sampling frequency of pulse wave data. When, for example, a pulse rate in one minute is to be obtained, pulse rate (i) at time i is obtained by the equation below.

$$\text{pulse rate } (i) = 60(\text{seconds}) \times \text{sampling frequency/average value of pulse wave intervals} \quad (13)$$

By the equation below, the pulse rate correction unit 701 calculates a difference between obtained pulse rate (i) and pulse rate (i−1), which was obtained previously.

$$\text{difference between pulse rates} = |\text{pulse rate } (i) - \text{pulse rate } (i-1)| \quad (14)$$

When the difference between pulse rates (pulse rate difference) is smaller than threshold value C (for instance two pulses), the pulse rate correction unit 701 outputs pulse rate (i) as it is. When the pulse rate difference is equal to or greater than threshold value C, the pulse rate correction unit 701 corrects pulse rate (i) by using, for example, coefficients α and β in the equation below.

$$\text{pulse rate } (i) = \alpha \times \text{pulse rate } (i) + \beta \times \text{pulse rate } (i-1) \quad (15)$$

$$\alpha + \beta = 1.0 \quad (16)$$

$$0.0 < \alpha < 1.0 \quad (17)$$

$$0.0 < \beta < 1.0 \quad (18)$$

The correction of pulse rates described above prevents the changing ratio of an average of pulse wave intervals from becoming an extremely great value.

Figure 9:
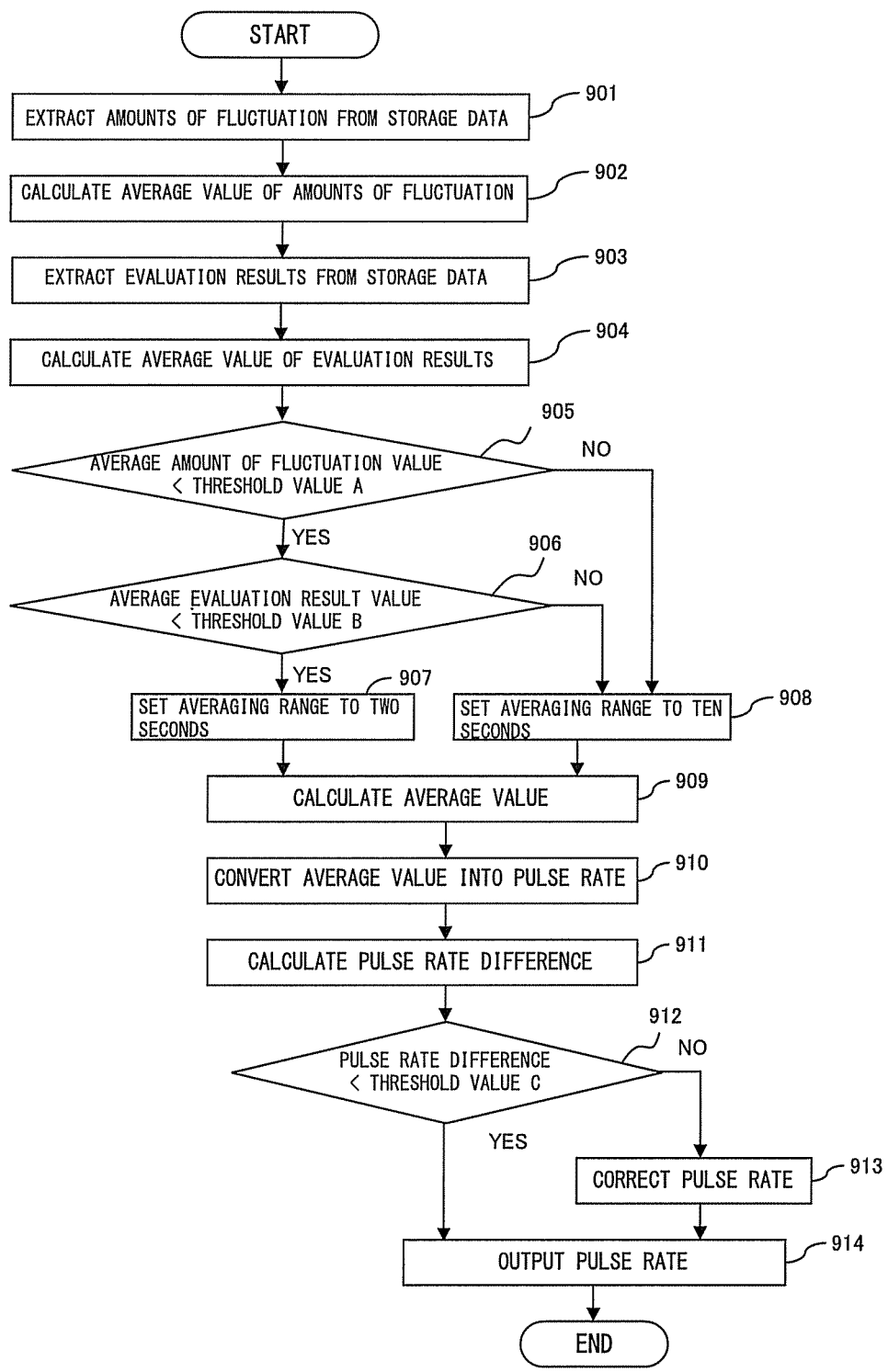
FIG. 9 illustrates a flowchart for a process executed by a pulse rate measuring apparatus.

FIG. 9 is a flowchart for an exemplary process executed by the averaging range determination unit 606, the average value calculation unit 607, the pulse rate conversion unit 608, and the pulse rate correction unit 701 illustrated in FIG. 8.

The averaging range determination unit 606 extracts amounts of fluctuation in a particular period (such as two seconds) from the data storage unit 605 (step 901), and calculates an average value of the amounts of fluctuation (step 902). Next, the averaging range determination unit 606 extracts the evaluation results of pulse wave intervals in a particular period from the data storage unit 605 (step 903), and calculates an average value of the evaluation results (step 904).

Next, the average value of amount of fluctuation and threshold value A are compared with each other (step 905). When the average value is equal to or greater than threshold value A, the averaging range is set to ten seconds (step 908). When the average value is smaller than threshold value A, the average value of the evaluation results is compared with threshold value B (step 906). When the average value of evaluation results is equal to or greater than threshold value B, the averaging range is set to ten seconds (step 908), and when the average value of evaluation results is smaller than threshold value B, the averaging range is set to two seconds (step 907). It should be understood that although the time periods set as the averaging ranges are two seconds and ten seconds respectively in steps 907 and 908, the averaging ranges are not limited to those values, and any value that is greater (longer time period) than a value set in step 907 can be set in step 908.

Next, the average value calculation unit 607 extracts from the data storage unit 605 pulse wave intervals in the averaging range that has been set, and calculates an average value of the pulse wave intervals (step 909). The pulse rate conversion unit 608 converts the calculated average value of pulse wave intervals into a pulse rate (step 910).

Next, the pulse rate correction unit 701 calculates a pulse rate difference by using equation (14) (step 911), and compares the calculated value with threshold value C (step 912). When the pulse rate difference is smaller than threshold value C, the pulse rate correction unit 701 outputs the pulse rate as it is (step 914). When the pulse rate difference is equal to or greater than threshold value C, the pulse rate correction unit 701 corrects the pulse rate (step 913), and outputs the corrected pulse rate (step 914).

Figure 10:
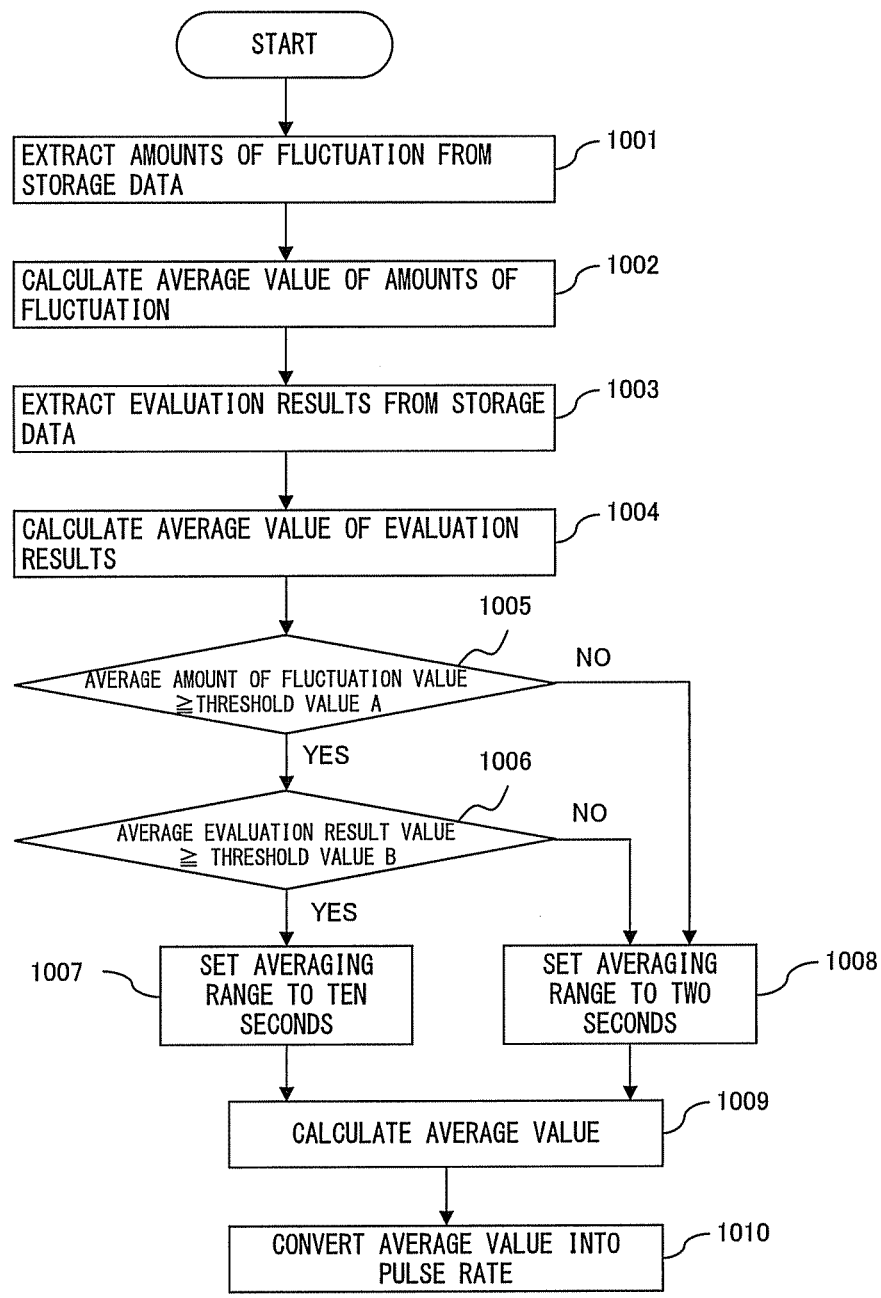
FIG. 10 is a flowchart for a first averaging range determination process.

FIG. 10 is a flowchart for a first variation example of the averaging range determination process. The processes executed in steps 1001 through 1004, 1009, and 1010 are similar to those executed in steps 901 through 904, 909, and 910 in FIG. 9.

The averaging range determination unit 606 compares an average value of amounts of fluctuation and threshold value A (step 1005). When the average value of amounts of fluctuation is smaller than threshold value A, the averaging range determination unit 606 sets the averaging range to two seconds (step 1008). When the average value of amounts of fluctuation is equal to or greater than threshold value A, the averaging range determination unit 606 compares the average value of the evaluation results with threshold value B (step 1006). When the average value of the evaluation results is smaller than threshold value B, the averaging range determination unit 606 sets the averaging range to two seconds (step 1008), and when the averaging value of the evaluation results is equal to or greater than threshold value B, the averaging range determination unit 606 sets the averaging range to ten seconds (step 1007). It should be understood that although the time periods set as the averaging ranges are ten seconds and two seconds respectively in steps 1007 and 1008, the averaging ranges are not limited to those values, and any value that is smaller (shorter time period) than a value set in step 1007 can be set in step 1008.

Figure 11:
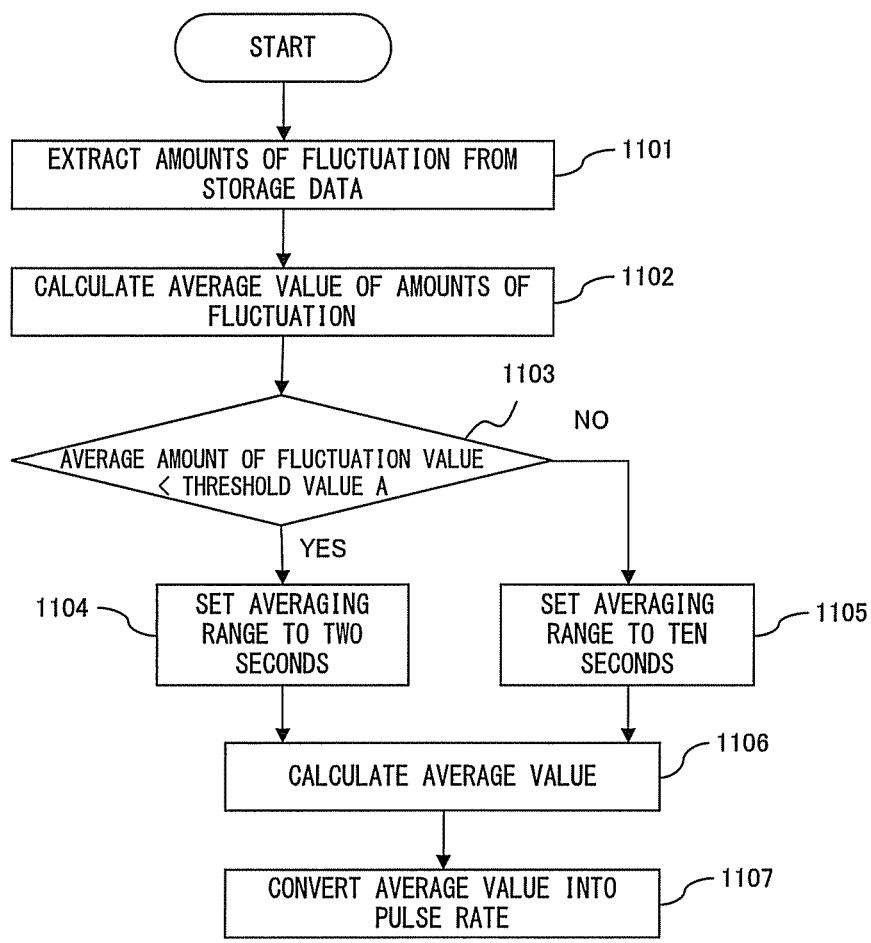
FIG. 11 is a flowchart for a second averaging range determination process.

FIG. 11 is a flowchart for a second variation example of the averaging range determination process. In this process, an averaging range is determined only on the basis of amounts of fluctuation. The processes executed in steps 1101, 1102, 1106, and 1107 are similar to those executed in steps 901, 902, 909, and 910 in FIG. 9.

The averaging range determination unit 606 compares an average value of amounts of fluctuation and threshold value A (step 1103). When the average value of amounts of fluctuation is equal to or greater than threshold value A, the averaging range determination unit 606 sets the averaging range to ten seconds (step 1105). When the average value of amounts of fluctuation is smaller than threshold value A, the averaging range determination unit 606 sets the averaging range to two seconds (step 1104). It should be understood that although the time periods set as the averaging ranges are two seconds and ten seconds respectively in steps 1104 and 1105, the averaging ranges are not limited to those values, and any value that is greater (longer time period) than a value set in step 1104 can be set in step 1105.

FIG. 12 is a flowchart for a third variation example of the averaging range determination process. In this process, an averaging range is determined only on the basis of evaluation results. The processes executed in steps 1201, 1202, 1206, and 1207 are similar to those executed in steps 903, 904, 909, and 910 in FIG. 9.

The averaging range determination unit 606 compares an average value of amounts of fluctuation with threshold value B (step 1203). When the average value of amounts of fluctuation is equal to or greater than threshold value B, the averaging range determination unit 606 sets the averaging range to ten seconds (step 1205). When the average value of amounts of fluctuation is smaller than threshold value B, the averaging range determination unit 606 sets the averaging range to two seconds (step 1204). It should be understood that although the time periods set as the averaging ranges are two seconds and ten seconds respectively in steps 1204 and 1205, the averaging ranges are not limited to those values, and any value that is greater (longer time period) than a value set in step 1204 can be set in step 1205.

FIG. 13 is a flowchart for a fourth variation example of the averaging range determination process. In this process, whether or not to use amounts of fluctuation for determination of an averaging value is determined on the basis of evaluation results. The processes executed in steps 1309 and 1310 are similar to those executed in steps 909 and 910 in FIG. 9.

The averaging range determination unit 606 extracts evaluation results of pulse wave intervals in a particular period from the data storage unit 605 (step 1301), and calculates an average value of the evaluation results (step 1302). Next, the averaging range determination unit 606 compares the average value of the evaluation results with threshold value B (step 1303), and sets the averaging value to ten seconds when the average value of the evaluation results is equal to or greater than threshold value B (step 1308).

When the average value of the evaluation results is smaller than threshold value B, amounts of fluctuation in a particular period are extracted from the data storage unit 605 (step 1304), and the average value of the amounts of fluctuation is calculated (step 1305).

Next, the average value of the amounts of fluctuation is compared with threshold value A (step 1306), and when the average value of the amounts of fluctuation is equal to or greater than threshold value A, the averaging range is set to ten seconds (step 1308). When the average value of the amounts of fluctuation is smaller than threshold value A, the averaging range is set to two second (step 1307). It should be understood that although the time periods set as the averaging ranges are two seconds and ten seconds respectively in steps 1307 and 1308, the averaging ranges are not limited to those values, and any value that is greater (longer time period) than a value set in step 1307 can be set in step 1308.

In the processes illustrated in FIGS. 9 through 13, the averaging ranges are set to ten or two seconds, however, "ten seconds" is just an example of a relatively wide averaging range, and "two seconds" is just an example of a relatively narrow averaging range. Accordingly, averaging ranges can be set to different values.

Also, the results of evaluation of the pulse wave interval and threshold values are compared in the processes illustrated in FIGS. 9, 10, 12, and 13, however, when the evaluation results are expressed in the form of flags such as "0" or "1", the determination based on threshold values can be skipped. In such a case, average values of evaluation results are not calculated, and whether a current evaluation result is "0" or "1" is determined in steps 906, 1006, 1203, and 1303.

When the evaluation result is "0", the processes in and subsequent to steps 907, 1007, 1204, and 1304 are executed. When the evaluation result is "1", the processes in and subsequent to steps 908, 1008, 1205, and 1308 are executed.

The processes executed by the respective units in the pulse rate measuring apparatuses illustrated in FIGS. 4 and 5 are similar to those executed by the corresponding units in the pulse rate measuring apparatus illustrated in FIG. 8. The averaging range determination unit 405 in FIG. 4 determines averaging ranges according to, for example, the flowchart in FIG. 11. The averaging range determination unit 504 in FIG. 5 determines averaging ranges according to, for example, the flowchart in FIG. 12.

When the processes executed by the pulse rate measuring apparatuses illustrated in FIGS. 4 through 6 and 8 are to be implemented by means of software, information processing equipment (computer) as illustrated in FIG. 14 is used. The information processing equipment illustrated in FIG. 14 includes a CPU (central processing unit) 1401, a memory device 1402, an input device 1403, an output device 1404, an external storage unit 1405, a medium driving device 1406, and a network connection device 1407, which are connected to one another via a bus 1408.

Examples of the memory device 1402 are a ROM (read only memory) device, a RAM (random access memory) device, etc. They store programs and data used for executing the processes. The CPU 1401 executes the programs utilizing the memory device 1402 in order to execute processes similar to those executed by the pulse rate measuring apparatuses.

Examples of the input device 1403 are a keyboard, a pointing device, and the like, and they are for inputting instructions and information from operating persons. Examples of the output device 1404 are a display device, a printer, a speaker, and the like, and they are for outputting questions and processing results to operating persons.

Examples of the external storage device 1405 are a magnetic disk device, an optical disk device, a magneto-optical disk device, a tape device, and the like. The information processing equipment stores programs and data in the external storage device 1405, and loads them into the memory device 1402 in order to use them as necessary.

The medium driving device 1406 drives a portable storage medium 1409 in order to access storage content in the portable storage medium 1409. The portable storage medium 1409 is an arbitrary computer-readable storage medium such as a memory card, a flexible disk, an optical disk, a magneto-optical disk, or the like. Operating persons store programs and data in the portable storage medium 1409, and load them into the memory device 1402 in order to use them as necessary.

The network connection device 1407 is connected to a communications network such as a LAN (local area network) or the like, and performs data conversion necessary for communications. The information processing equipment receives programs and data from external devices via the network connection device 1407, and loads them into the memory device 1402 in order to use them as necessary.

FIG. 15 shows a manner of providing programs and data to the information processing equipment illustrated in FIG. 14. The programs and data stored in the portable storage medium 1409 and database 1511 in an external device 1501 are loaded into the memory device 1402 in information processing equipment 1502. The external device 1501 generates carrier signals for carrying the programs and data, and transmits the signals to the information processing equipment 1502 via an arbitrary transmission medium on the communications network. The CPU 1401 uses the data to execute the programs in order to execute the above processes.

According to the pulse rate measuring apparatuses as disclosed above, it is possible to output a pulse rate stably with reduced influence by a disturbance caused when the examinee is exercising, and also to accurately output slight variations in a pulse rate when the examinee is staying quiet, with reduced delay time.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A pulse rate measuring apparatus, comprising:
   a first calculation device for receiving input of pulse wave data obtained from change in a blood flow, and calculating an average interval of a prescribed number of immediately preceding pulses or pulses in an immediately preceding prescribed time period;
   a determination device for determining an average-calculation range for calculating an average value based on at least one of an amount of fluctuation and an evaluation result, the amount of fluctuation being a value calculated based on a difference between the average interval and an interval of a pulse wave newly detected from the pulse wave data, and the evaluation result being a result of evaluating the interval of the newly detected pulse wave by at least one evaluation factor, wherein when the amount of fluctuation is greater than a prescribed value, the determination device determines the average-calculation range to be wider than the average-calculation range determined when the amount of fluctuation is smaller than the prescribed value;
   a second calculation device for averaging pulse wave intervals of the pulse wave data based on the average-calculation range, and calculating an average pulse wave interval value; and
   a third calculation device for calculating a pulse rate based on the average pulse wave interval value.

2. The pulse rate measuring apparatus according to claim 1, wherein:

when a difference between the interval of the newly detected pulse wave and an interval of an immediately preceding pulse or the average interval is greater than a threshold value, the determination device determines the average-calculation range to be wider than a range determined when the difference is smaller than the threshold value.

3. The pulse rate measuring apparatus according to claim 1, wherein:

when a minimum value of one of the pulse wave data, difference data of the pulse wave data, and secondary difference data of the pulse wave data is greater than a threshold value, the determination device determines the average-calculation range to be wider than a range determined when the minimum value is smaller than the threshold value.

4. The pulse rate measuring apparatus according to claim 1, wherein:

when a maximum value of one of the pulse wave data, difference data of the pulse wave data, and secondary difference data of the pulse wave data is smaller than a threshold value, the determination device determines the average-calculation range to be wider than a range determined when the maximum value is greater than the threshold value.

5. The pulse rate measuring apparatus according to claim 1, wherein:

when an autocorrelation value of one of the pulse wave data, difference data of the pulse wave data, and secondary difference data of the pulse wave data is smaller than a threshold value, the determination device determines the average-calculation range to be wider than a range determined when the autocorrelation value is greater than the threshold value.

6. The pulse rate measuring apparatus according to claim 1, wherein:

when a difference ratio or a difference changing ratio between the interval of the newly detected pulse wave and an interval of a pulse wave in a normal state is greater than a threshold value, the determination device determines the average-calculation range to be wider than a range determined when the difference ratio or the difference changing ratio is smaller than the threshold value.

7. The pulse rate measuring apparatus according to claim 1, further comprising:

a correction device for correcting, when a difference between the pulse rate calculated by the third calculation device and a pulse rate calculated for an immediately preceding pulse is equal to or greater than a threshold value, the pulse rate calculated by the third device using the pulse rate calculated for the immediately preceding pulse.

8. A storage medium storing a program causing a computer to execute:

receiving input of pulse wave data obtained from change in a blood flow, and calculating an average interval of a prescribed number of immediately preceding pulses or pulses in an immediately preceding prescribed time period;

determining an average-calculation range for calculating an average value on the basis of at least one of an amount of fluctuation and an evaluation result, the amount of fluctuation being a value calculated on the basis of a difference between the average interval and an interval of a pulse wave newly detected from the pulse wave data, and the evaluation result being a result of evaluating the interval of the newly detected pulse wave by at least one evaluation factor, wherein when the amount of fluctuation is greater than a prescribed value, the average-calculation range is determined to be wider than the average-calculation range determined when the amount of fluctuation is smaller than the prescribed value;

averaging pulse wave intervals of the pulse wave data on the basis of the average-calculation range, and calculating an average pulse wave interval value; and calculating a pulse rate on the basis of the average pulse wave interval value.

9. A pulse rate measuring apparatus, comprising:

first calculation means for receiving input of pulse wave data obtained from change in a blood flow, and calculating an average interval of a prescribed number of immediately preceding pulses or pulses in an immediately preceding prescribed time period;

determination means for determining an average-calculation range for calculating an average value on the basis of at least one of an amount of fluctuation and an evaluation result, the amount of fluctuation being a value calculated on the basis of a difference between the average interval and an interval of a pulse wave newly detected from the pulse wave data, and the evaluation result being a result of evaluating the interval of the newly detected pulse wave by at least one evaluation factor;

second calculation means for averaging pulse wave intervals of the pulse wave data on the basis of the average-calculation range, and calculating an average pulse wave interval value; and third calculation means for calculating a pulse rate on the basis of the average pulse wave interval value.

* * * * *